(12) United States Patent
Yu et al.

(10) Patent No.: US 11,783,189 B2
(45) Date of Patent: Oct. 10, 2023

(54) ADVERSARIAL COOPERATIVE IMITATION LEARNING FOR DYNAMIC TREATMENT

(71) Applicant: NEC Laboratories America, Inc., Princeton, NJ (US)

(72) Inventors: Wenchao Yu, Plainsboro, NJ (US); Haifeng Chen, West Windsor, NJ (US)

(73) Assignee: NEC Corporation

( * ) Notice: Subject to any disclaimer, the term of this patent is extended or adjusted under 35 U.S.C. 154(b) by 591 days.

(21) Appl. No.: 16/998,228

(22) Filed: Aug. 20, 2020

(65) Prior Publication Data

US 2021/0065009 A1    Mar. 4, 2021

Related U.S. Application Data

(60) Provisional application No. 62/893,324, filed on Aug. 29, 2019.

(51) Int. Cl.
*G06N 3/08* (2023.01)
*G06N 3/084* (2023.01)
*G16H 50/30* (2018.01)
*G06N 20/20* (2019.01)
*G06N 5/046* (2023.01)
*G06N 3/045* (2023.01)

(52) U.S. Cl.
CPC .......... *G06N 3/084* (2013.01); *G06N 3/045* (2023.01); *G06N 5/046* (2013.01); *G06N 20/20* (2019.01); *G16H 50/30* (2018.01)

(58) Field of Classification Search
CPC ...... G06N 3/02; G06N 3/0455; G06N 3/0475; G06N 3/08; G06N 3/09–094; G06N 20/00; G16H 50/30
See application file for complete search history.

(56) References Cited

U.S. PATENT DOCUMENTS

2018/0307995 A1* 10/2018 Conroy ................. G06N 20/10
2018/0333106 A1* 11/2018 Roberts ................. G16H 50/30

OTHER PUBLICATIONS

Luo et al. "Discriminative apprenticeship learning with both preference and non-preference behavior", 2013, 12th International Conference on Machine Learning and Applications.*
Wang et al. "Robust Imitation of Diverse Behaviors", 2017, 31st Conference on Neural Information Processing System.*

(Continued)

*Primary Examiner* — Jue Louie
(74) *Attorney, Agent, or Firm* — Joseph Kolodka

(57) ABSTRACT

Methods and systems for responding to changing conditions include training a model, using a processor, using trajectories that resulted in a positive outcome and trajectories that resulted in a negative outcome. Training is performed using an adversarial discriminator to train the model to generate trajectories that are similar to historical trajectories that resulted in a positive outcome, and using a cooperative discriminator to train the model to generate trajectories that are dissimilar to historical trajectories that resulted in a negative outcome. A dynamic response regime is generated using the trained model and environment information. A response to changing environment conditions is performed in accordance with the dynamic response regime.

16 Claims, 7 Drawing Sheets

(56) References Cited

OTHER PUBLICATIONS

Gujar "Quick Introduction to GANs", Mar. 31, 2018, retrieved from: https://medium.com/@sanketgujar95/quick-introduction-to-gans-1d1f099dc4a7.*

Wang et al. "Supervised Reinforcement Learning with Recurrent Neural Network for Dynamic Treatment Recommendation", Aug. 19-23, 2018, KDD '18: Proceedings of the 24th ACM SIGKDD International Conference on Knowledge Discovery & Data Mining.*

Yu et al. "Inverse reinforcement learning for intelligent mechanical ventilation and sedative dosing in intensive care units", Apr. 9, 2019, BMC Medical Informatics and Decision Making.*

Cheng et al. "Extubation Decision Making with Predictive Information for Mechanically Ventilated Patients in ICU", Jun. 13, 2019, retrieved from: https://ssrn.com/abstract=3397530.*

Duan et al., "One-shot imitation learning", 31st Conference on Neural Information Processing Systems. Advances in neural information processing systems. Dec. 4-9, 2017. pp. 1087-1098.

Finn et al., "Guided cost learning: Deep inverse optimal control via policy optimization", International Conference on Machine Learning. Jun. 11, 2016. pp. 49-58.

Goodfellow et al., "Generative adversarial nets", Advances in neural information processing systems. Dec. 8-13, 2014. pp. 2672-2680.

Grollman et al., "Donut as i do: Learning from failed demonstrations", IEEE International Conference on Robotics and Automation. May 14, 2011. pp. 3804-3809.

Ho et al., "Generative adversarial imitation learning", 30th Conference on Advances in neural information processing systems. Dec. 5-10, 2016. pp. 4565-4573.

Jin et al., "A treatment engine by predicting next-period prescriptions", Proceedings of the 24th ACM SIGKDD International Conference on Knowledge Discovery & Data Mining. Jul. 19, 2018. pp. 1608-1616.

Jin et al., "Real-Time Bidding with Multi-Agent Reinforcement Learning in Display Advertising", Proceedings of the 27th ACM International Conference on Information and Knowledge Management 2018. arXiv:1802.09756v2 [stat.ML] Sep. 11, 2018. pp. 1-10.

Kingma et al., "Auto-encoding variational bayes", arXiv:1312.6114v10 [stat.ML] May 1, 2014. pp. 1-14.

Komorowski et al. "The artificial intelligence clinician learns optimal treatment strategies for sepsis in intensive care", Nature Medicine. Nov. 2018. vol. 24, No. 11. p. 1-11.

Li et al., "Infogail: Interpretable imitation learning from visual demonstrations", Advances in Neural Information Processing Systems. Dec. 4-9, 2017. pp. 3812-3822.

Murphy et al., "Optimal dynamic treatment regimes", Journal of the Royal Statistical Society: Series B (Statistical Methodology). Jan. 28, 2003. vol. 65, No. 2. pp. 331-355.

Pomerleau et al. "Efficient training of artificial neural networks for autonomous navigation", Neural Computation, Mar. 1991. vol. 3, No. 1. pp. 88-97.

Raghu et al. "Continuous state-space models for optimal sepsis treatment—a deep reinforcement learning approach", arXiv:1705.08422v1 [cs.LG] May 23, 2017. pp. 1-17.

Ross et al., "Efficient reductions for imitation learning", Proceedings of the thirteenth international conference on artificial intelligence and statistics. May 13-15, 2010. vol. 9 of JMLR:W&CP9. pp. 661-668.

Ross et al., "A reduction of imitation learning and structured prediction to no-regret online learning", Proceedings of the fourteenth international conference on artificial intelligence and statistics. Jun. 14, 2011. pp. 627-635.

Saria, S., "Individualized sepsis treatment using reinforcement learning", Nov. 2018. Nature medicine, vol. 24, No. 11. p. 1641-1642.

Sulton et al., "Introduction to reinforcement learning", MIT press Cambridge, Mar. 1, 1998. vol. 2. pp. 1-20.

Van Der Pol et al., "Coordinated deep reinforcement learners for traffic light control", Proceedings of Learning, Inference and Control of Multi-Agent Systems (at NIPS, Aug. 2016). pp. 1-8.

Wang et al., "Supervised reinforcement learning with recurrent neural network for dynamic treatment recommendation", Proceedings of the 24th ACM SIGKDD International Conference on Knowledge Discovery & Data Mining 2018. arXiv:1807.01473v2 [cs.LG], Sep. 17, 2018. pp. 1-10.

Wulfmeier et al., "Maximum entropy deep inverse reinforcement learning", exarXiv:1507.04888v3 [cs.LG]. Mar. 11, 2016.

Zhang et al., "Leap: learning to prescribe effective and safe treatment, combinations for multimorbility", Proceedings of the 23rd ACM SIGKDD International Conference on Knowledge Discovery and Data Mining. Aug. 13-17, 2017. pp. 1315-1324.

Zheng et al., "DRN: a deep reinforcement learning framework for news recommendation", Proceedings of the 2018 World Wide Web Conference. Apr. 23-27, 2018. International World Wide Web Conferences Steering Committee. pp. 167-176.

Zhifei et al. "A survey of inverse reinforcement learning techniques", International Journal of Intelligent Computing and Cybernetics. Aug. 17, 2012. vol. 5, No. 3. pp. 293-311.

Ziebart et al., "Maximum entropy inverse reinforcement learning", Proceedings of the Twenty-Third AAAI Conference on Artificial Intelligence. Feb. 2-7, 2018. pp. 1433-1488.

Abbeel et al, "Apprenticeship learning via inverse reinforcement learning", Proceedings of the twenty-first international conference on Machine learning. Jul. 4, 2004. pp. 1-8.

Bajor et al., "Predicting medications from diagnostic codes with recurrent neural networks", International Conference on Learning Representations. Apr. 24-26, 2017. pp. 1-19.

Bothe et al., "The use of reinforcement learning algorithms to meet the challenges of an artificial pancreas", Expert review of medical devices. Apr. 10, 2014. vol. 10, No. 5. pp. 661-673.

Buesing et al., "Learning and querying fast generative models for reinforcement learning", arXiv:1802.03006v1 [cs.LG]. Feb. 8, 2018. pp. 1-15.

Chakraborty et al., "Dynamic treatment regimes", Annual review of statistics and its application. Jan. 3, 2014. pp. 447-464.

Chen et al., "Generative Adversarial User Model for Reinforcement Learning Based Recommendation System", International Conference on Machine Learning. May 24, 2019. pp. 1052-1061.

Choi et al., "Doctor ai: Predicting clinical events via recurrent neural networks". Machine Learning for Healthcare Conference. Dec. 10, 2016. pp. 301-318.

Co-Reyes et al., "Self-Consistent Trajectory Autoencoder: Hierarchical Reinforcement Learning with Trajectory Embeddings", International Conference on Machine Learning. arXiv:1806.02813v1 [cs.LG], Jun. 7, 2018. pp. 1008-1017.

Dudik et al., "Doubly Robust Policy Evaluation and Learning", arXiv:1103.4601 v2 [cs.LG], May 6, 2011. pp. 1-9.

Gu et al., "Deep reinforcement learning for robotic manipulation with asynchronous off-policy updates", arXiv:1610.006332 [cs.RO]. Nov. 23, 2016. pp. 1-9.

Jiang et al., "Doubly robust off-policy value evaluation for reinforcement learning", International Conference on Machine Learning. Jun. 11, 2016. pp. 652-661.

Johnson et al., "MIMIC-III, a freely accessible critical care database", Scientific Data. vol. 3, No. 1. May 24, 2016. pp. 1-9.

Van Der Maaten et al., "Visualizing data using t-SNE", Journal of machine learning research. Nov. 9, 2008. pp. 2579-2605.

Precup et al., "Off-policy temporal-difference learning with function approximation" 18th International Conference of Machine Language. Jun. 28-Jul. 1, 2001. pp. 417-424.

Raghu et al., "Deep reinforcement learning for sepsis treatment", arXiv:1711.09602v1 [cs.AI]. Nov. 27, 2017. pp. 1-9.

Singer et al., "The third international consensus definitions for sepsis and septic shock (Sepsis-3)", Jama. vol. 315, No. 8. Feb. 23, 2016. pp. 801-810.

* cited by examiner

Require: Positive and negative trajectories $\tau^+$ and $\tau^-$ generated by behavior policies $\pi_+$ and $\pi_-$, batch $\mathcal{B}$, horizon $T$, mini-batch size $N$, episode size $M$. Initial the parameters of $\pi_\theta$, $D_a$, $D_c$ and $G_w = \{E_{w_1}, D_{w_2}\}$.

1: for $t = 1$ to $T$ do
2:    Sample mini-batch of N transitions from both $\tau^+$ and $\tau^-$ $(s_t, a_t, s_{t+1})$ from $\mathcal{B}$
3:    $\mu, \sigma = E_{w_1}(s_t, a_t)$, $\bar{s}_{t+1} = D_{w_2}(s_t, a_t, z), z \sim \mathcal{N}(\mu, \sigma)$
4:    Update $w$ with Eq. (8).
5: end for
6: for *episode* $= 0$ to $M$ do
7:    Sample trajectories $\tau_i \sim \pi_\theta$, $\tau_i^+ \sim \pi_+$, $\tau_i^- \sim \pi_-$ ;
8:    Update the parameters of $D_a$ with $\tau^+$, $\tau^\theta$ and the gradient $\hat{\mathbb{E}}_{\tau_i^\theta}[\nabla \log(1 - D_a(s, a))] + \hat{\mathbb{E}}_{\tau_i^+}[\nabla \log(D_a(s, a))]$, where $\hat{\mathbb{E}}_\tau$ presents the estimated expectation with $\tau$.
9:    Update the parameters of $D_s$ with $\tau^+$, $\tau^-$, $\tau^\theta$ and the gradient $\hat{\mathbb{E}}_{\tau_i^\theta, \tau_i^+}[\nabla \log(D_c(s, a))] + \hat{\mathbb{E}}_{\tau_i^-}[\nabla \log(1 - D_c(s, a))]$.
10:    Update the parameters of $\pi_\theta$ using TRPO with the cost function $\omega_\alpha \log(D_a(s, a)) + \omega_\beta \log(D_s(s, a))$. Specifically, $\theta$ is updated by the gradient,
$\hat{\mathbb{E}}_{\tau_i^\theta}[\nabla_\theta \log \pi_\theta(a|s) Q(s, a)] - \lambda \nabla_\theta H(\pi_\theta)$,
where $Q(s, a) = \hat{\mathbb{E}}_{\tau_i^\theta}[\omega_\alpha \log(D_a(s, a) + \omega_\beta \log(D_s(s, a)]$.
11: end for

FIG. 4

ADVERSARIAL COOPERATIVE IMITATION LEARNING FOR DYNAMIC TREATMENT

RELATED APPLICATION INFORMATION

This application claims priority to U.S. Patent Application No. 62/893,324, filed on Aug. 29, 2019, incorporated herein by reference herein its entirety.

BACKGROUND

Technical Field

The present invention relates to providing medical treatments to patients, and, more particularly, to determining tailored treatments that are adjusted over time according to the changing state of the patients.

Description of the Related Art

Determining treatments for individual patients has historically been performed by highly skilled doctors, who apply their experience and training to assess the patient's needs and provide a course of treatment. However, the fallibility of human judgment leads to errors. As a result, there is a need to automate the process of medical decision-making, particularly as it applies to the modification of a treatment plan in response to changing patient conditions.

SUMMARY

A method for responding to changing conditions includes training a model, using a processor, using trajectories that resulted in a positive outcome and trajectories that resulted in a negative outcome. Training is performed using an adversarial discriminator to train the model to generate trajectories that are similar to historical trajectories that resulted in a positive outcome, and using a cooperative discriminator to train the model to generate trajectories that are dissimilar to historical trajectories that resulted in a negative outcome. A dynamic response regime is generated using the trained model and environment information. A response to changing environment conditions is performed in accordance with the dynamic response regime.

A method for treating a patient includes training a model on historical treatment trajectories, including trajectories that resulted in a positive health outcome and trajectories that resulted in a negative health outcome. A dynamic treatment regime is generated for a patient using the trained model and patient information. The patient is treated in accordance with the dynamic treatment regime, in a manner that is responsive to changing patient conditions, by triggering one or more medical devices to administer a treatment to the patient.

A system for treating a patient includes a machine learning model, configured to generate a dynamic response regime for using environment information. A model trainer is configured to train the machine learning model, including trajectories that resulted in a positive outcome and trajectories that resulted in a negative outcome, by using an adversarial discriminator to train the machine learning model to generate trajectories that are similar to historical trajectories that resulted in a positive outcome, and by using a cooperative discriminator to train the model to generate trajectories that are dissimilar to historical trajectories that resulted in a negative outcome. A response interface is configured to trigger a response to changing environment conditions in accordance with the dynamic response regime.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein:

FIG. 4 is pseudo-code for a learning process for a machine learning model to generate dynamic treatment regimes, in accordance with an embodiment of the present invention;

DETAILED DESCRIPTION OF PREFERRED EMBODIMENTS

Embodiments of the present invention provide a dynamic treatment regime (DTR), a sequence of tailored treatment decisions that specify how treatments should be adjusted through time, in accordance with the dynamic states of patients. Rules in the DTR can take input information, such as a patient's medical history, laboratory results, and demographic information, and output recommended treatments to improve the effectiveness of the treatment program.

The present embodiments can make use of deep reinforcement techniques for machine learning, for example to learn treatment policies from doctors' previous treatment plans. The present embodiments do so in such a way as to avoid the compounding errors that can result from supervised methods that are based on behavior cloning and the sparsity of self-defined reward signals in reinforcement learning models. Treatment paths are considered that include both positive trajectories, where a positive health outcome was achieved for a patient, and negative trajectories, where a negative health outcome resulted. By using both positive and negative trajectories, productive strategies are learned, and unproductive strategies are avoided.

Toward that end, the present embodiments use an adversarial cooperative imitation learning (ACIL) model to determine the dynamic treatment regimes that produce positive outcomes, while staying away from negative trajectories. Two discriminators can be used, including an adversarial discriminator and a cooperative discriminator. The adversarial discriminator minimizes the discrepancies between the output trajectories and the positive trajectories in a set of training data, while the cooperative discriminator distinguishes the negative trajectories from the positive trajectories and the output trajectories. Reward signals from the discriminators are used to refine the policy that generates dynamic treatment regimes.

Based on the policies learned by the model, DTRs are generated in response to specific patient information. These DTRs are then implemented, by providing the specified care and treatment to the patients, responsive to the changing condition for each patient. The present embodiments thereby reduce the likelihood of a negative health outcome and provide superior dynamic treatment regimens.

Figure 1:
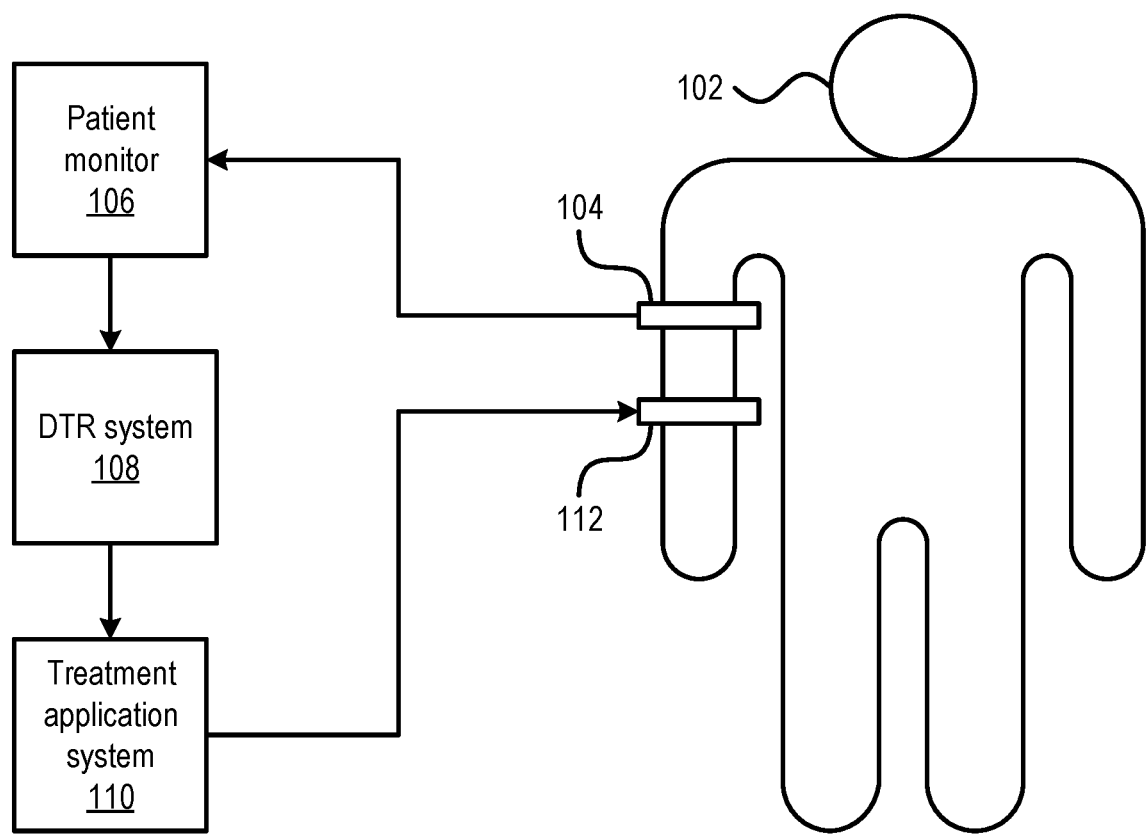
FIG. 1 is a block diagram showing a patient being monitored and treated by a system that uses a dynamic treatment regime to react to changing patient conditions, in accordance with an embodiment of the present invention.

Referring now to FIG. 1, an embodiment of the present invention is shown. A patient 102 is shown. The patient 102 may, for example, have a medical condition that is being treated. One or more sensors 104 monitor information about the patient's condition, and provide the information to patient monitor 106. This information may include vital information, such as heart rate, blood oxygen saturation, blood pressure, body temperature, blood sugar levels. The information may also include patient activity information, such as movements and location. In each case, the information may be collected by any appropriate sensing device or device(s) 104. The patient monitor 106 may also accept information about the patient that is not sensed directly, for example including the patient's demographic information (e.g., age, medical history, family medical history, etc.) and the patient's own statement of symptoms, for example input by the patient or collected by a medical professional.

The patient monitor 106 renders the collected information in a format suitable for the DTR system 108. The DTR system 108 includes a set of rules for how treatment should progress, based on updates to the patient's monitored information. As just one example of such a rule, if a patient's blood pressure were to drop below a threshold, the DTR system 108 may indicate an appropriate medical response and adjustment to treatment. The DTR system's policies are learned in advance, as described in greater detail below, to incorporate past instances of successful and unsuccessful treatments, thereby providing a set of rules that stay close to successful treatment trajectories, while staying away from unsuccessful treatment trajectories.

A treatment application system 110 accepts directives from the DTR system 108 and takes an appropriate action. In some cases, when the treatment recommendation involves the intervention of a medical professional, the treatment system 110 can output an alert or an instruction for the recommended treatment. In other cases, the treatment recommendation can include an automatic treatment intervention, by way of one or more medical treatment devices 112. As just one example of such an automatic treatment, if the DTR system 108 indicates that a patient's dropping blood pressure necessitates a quick pharmaceutical intervention, the treatment system 110 may cause a treatment device to introduce an appropriate medication to the patient's bloodstream.

In this manner, the present embodiments can make rapid adjustments to a patient's treatment, responsive to the patient's changing medical condition. This reduces the reliance on fallible human decision-making and can lead to superior outcomes, particularly in stressful situations, where a decision needs to be made quickly and correctly.

Figure 2:
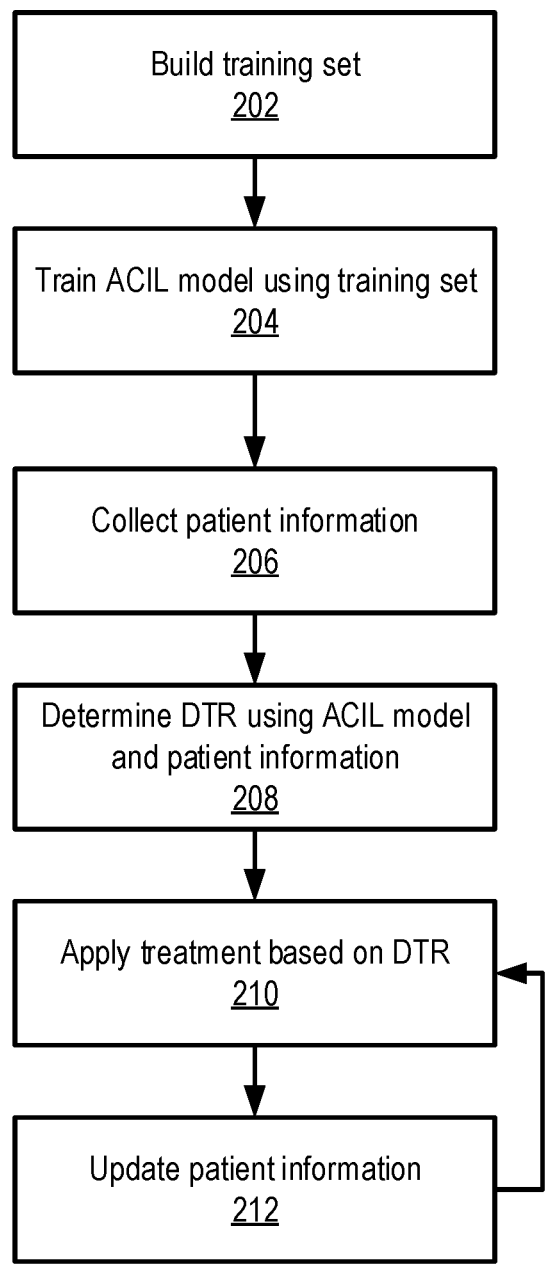
FIG. 2 is a block/flow diagram of a method for generating and implementing a dynamic treatment regime for a patient, in accordance with an embodiment of the present invention.

Referring now to FIG. 2, a method of treating a patient is shown. Block 202 builds a set of training data that includes, for example, records of historical treatment trajectories. The historical treatment trajectories may include information about patient condition, information about the timing and type of treatment actions and changes, and information about the treatment's outcome. Treatment trajectories with both positive health outcomes and negative health outcomes are included in the training set.

In some embodiments, the trajectories can be represented as sequences of states and actions $(s_0, a_0, s_1, a_1, \ldots)$ drawn from a policy $\pi$. Thus, each state $s_t \in \mathcal{S}$ includes collected patient information at a time t, and each action $a_t \in \mathcal{A}$ includes a K-dimensional binary-valued vector, where the value on each dimension represents the application of a particular medication, dosage, or treatment action. Some of the trajectories are associated with policies that result in positive outcomes $(\pi_+)$, while other trajectories are associated with policies that result in negative outcomes $(\pi_-)$. The positive trajectories can be expressed as $\tau^+ = (s_1^+, a_1^+, \ldots)$ and the negative trajectories can be expressed as $\tau^- = (s_1^-, a_1^-, \ldots)$.

Block 204 then uses the training set to train the ACIL model. This model may be implemented using machine learning techniques, described in greater detail below. The model accepts patient information as an input, and outputs one or more DTR policies for the patient. As noted above, a DTR policy includes one or more rules that are used to adapt treatment to changing patient conditions.

Block 206 then collects information for a specific patient 102, as described above. In block 208, the patient information is used as an input to the ACIL model to produce a DTR policy for the specific patient 102, relating to that patient's treatment needs. The output policy can be expressed as $\pi_\theta$, with a parameter vector $\theta$ that represents the particular policy rules. Block 210 then applies a recommended treatment to the patient 102, using the collected patient information, following a trajectory $\tau_\theta$ that is generated by the policy $\pi_\theta$. As time goes on, block 212 updates the patient information, for example with current measurements. Block 210 then uses this updated information to determine any updated treatments that may be needed, according to the DTR. This process can continue indefinitely, or can be interrupted by a positive or negative health outcome.

Figure 3:
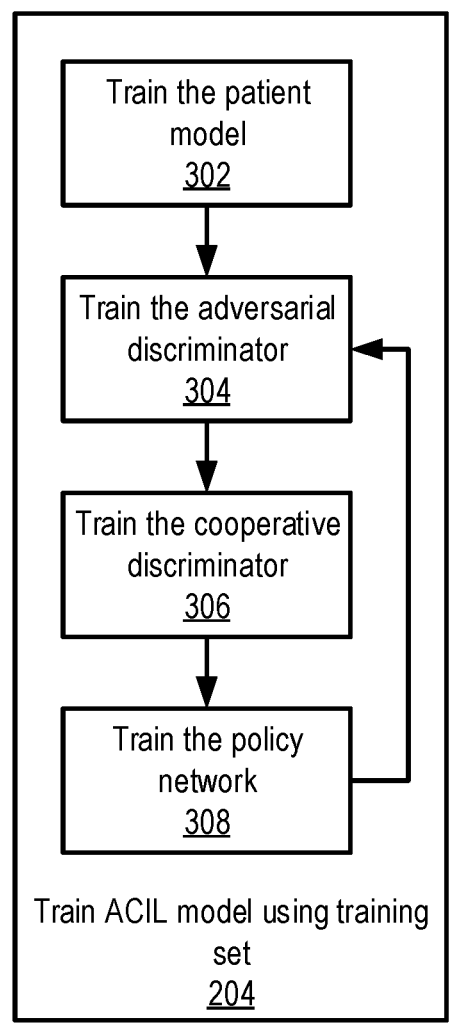
FIG. 3 is a block/flow diagram of a method for training a machine learning model to generate dynamic treatment regimes, in accordance with an embodiment of the present invention.

Referring now to FIG. 3, additional information on the training of the ACIL model in block 204 is shown. As an overview, block 302 trains the patient model, which serves as an environment simulator. The adversarial discriminator, cooperative discriminator, and policy network are then iteratively trained until they converge in blocks 304, 306, and 308. Convergence can be determined, for example, by determining that the improvement from one iteration to the next has fallen below a predetermined threshold. Alternatively, processing can stop when a predetermined number of iterations has been reached.

In block 302, the environment can be simulated with generative models, such as variational auto-encoders, for model-based reinforcement learning and trajectory embedding. As an alternative to using a variable auto-encoder, a generative adversarial network can be used instead. The variational auto-encoder architecture builds a patient model that transforms a state distribution into an underlying latent space. The patient model includes an encoder, which maps the current state and action to a latent distribution $z \sim \mathcal{N}(\mu, \sigma)$, and a decoder, which maps latent z and the current state $s_t$ and action $a_t$ into a successor state $\hat{s}_{t+1}$. The patient model is trained to minimize a reconstruction error between the input state $s_{t+1}$ and a reconstructed state $\hat{s}_{t+1}$ that is generated by the decoder, under the latent distribution z. An objective function for this can be expressed as:

$$\min_{w} \sum_{s_t, a_t, s_{(t+1)}} \|s_{t+1} - \hat{s}_{t+1}\|_2 + \alpha D_{KL}(\mathcal{N}(\mu, \sigma) \| \mathcal{N}(0, 1))$$

where w is a reconstruction error, $s_t$ is a state at time t, $a_t$ is an action at time t, $\mu$, $\sigma = E_{w_1}(s_t, a_t)$ is an encoder network that takes the current state $s_t$ and action $a_t$ as inputs, using a first parameter $w_1$, and $\hat{s}_{t+1} = D_{w_2}(s_t, a_t, z)$ is the output a decoder network $D_{w_2}$ with a latent factor z and the current state and action as input, using a second parameter $w_2$. The variable $\alpha$ represents a balancing weight between two kinds of loss, and the function $D_{KL}$ is the Kullback-Liebler divergence.

In general, the auto-encoder seeks to "encode" the input information, in this case the "actions" and "states," and translates them to the latent space. In some embodiments, this latent space may represent the actions and states as vectors, which can be readily compared to one another. The decoder then translates those vectors back to "actions" and "states," and an error w represents the difference between the output of the decoder and the input to the encoder. The parameters of the auto-encoder are then modified to reduce the value of the error. Training continues, with the parameters being modified at each iteration, until the error value reaches a point where no further training is needed. This may be triggered, for example, when the error value falls below a threshold, or when the error value does not change significantly over a number of iterations.

In block 304, training the adversarial discriminator includes a comparison between the trajectories of positive outcome scenarios and the trajectories generated by a policy network. In general, the differences between two policies (e.g., the policy $\pi_\theta$ generated by the ACIL model, and a policy with a positive outcome $\pi_+$) by comparing the trajectories they generate. For a policy $\pi \in \Pi$, the occupancy measure $\rho_\pi : S \times A \to \mathbb{R}$ can be defined as $\rho_\pi(s, a) = \pi(a|s) \Sigma_{t=0}^T \gamma^t P(s_t = s|\pi)$, where $\gamma$ is a discounting factor, T is a maximum time value, and where successor states are drawn from $P(s|\pi)$. The occupancy measure can be interpreted as the distribution of state-action pairs that the policy interacts with in the environment. A policy $\pi_\theta$ can be implemented as a multiple-layer perceptron network, where $\pi_\theta$ takes the state of the patient as an input and returns, for example, recommended medications.

The adversarial discriminator $D_a(s, a)$ can also be implemented as a multiple-layer perceptron network, having a number and dimension of layers that are fine-tuned parameters, which estimates the probability that a state-action pair $(s, a)$ comes from a positive trajectory policy $\pi_+$, rather than a generated policy $\pi_\theta$. The learning of the adversarial discriminator can be expressed as the following objective function:

$$\max_{D_a} \mathbb{E}_{\rho_{\pi_\theta}}[\log(1 - D_a(s, a))] + \mathbb{E}_{\rho_{\pi_+}}[\log(D_a(s, a))]$$

This objective function is equivalent to minimizing the Jensen-Shannon divergence $D_{JS}$ between the distributions of state-action pairs $\rho_{\pi_\theta}$ and $\rho_{\pi_+}$, which are generated by interacting with the environment using policy $\pi_\theta$ and policy $\pi_+$. $\mathbb{E}$ represents the expectation over all (s, a) pairs sampled from $\rho_{\pi_\theta}$. $D_a$ is referred to as an adversarial discriminator, because the goals of optimizing $D_a$ and $\pi_\theta$ are opposite-$D_a$ seeks to minimize the probability of the state-action pair generated by $\pi_\theta$, while $\pi_\theta$ is selected to maximize the probability of $D_a$ making a mistake.

In block 306, training the cooperative discriminator includes training a model to differentiate the generated trajectories and the positive trajectory policies from the negative trajectory policies. The occupancy measure $\rho_\pi$ can be used again to compare the different policies. The objective function for learning the cooperative discriminator $D_c$ can be expressed as:

$$\max_{D_c} \mathbb{E}_{\rho_{\pi_\theta}, \rho_{\pi_+}}[\log(D_c(s, a))] + \mathbb{E}_{\rho_{\pi_-}}[\log(1 - D_c(s, a))]$$

This objective function characterizes the optimal negative log loss of classifying the positive trajectories generated from $\pi_\theta$ and $\pi_+$ and the negative trajectories generated from $\pi_-$. This is referred to as a cooperative discriminator because the goals of $D_c$ and $\pi_\theta$ are both to maximize the probability of the data that is generated by $\pi_\theta$ is positive. The losses from $D_a$ and $D_c$ can be considered as reward functions that help refine $\pi_\theta$. When the distribution $\rho_{\pi_\theta}$ is different from $\rho_{\pi_-}$, it receives a large reward from $D_c$. With an optimal $D_c$, the loss of $\pi_\theta$ is $D_{JS}(\rho_{\pi_+} + \rho_{\pi_\theta} \| \rho_{\pi_-})$.

In block 308, training the policy network seeks to update the policy network $\pi_\theta$ to mimic positive trajectories, while staying away from negative trajectories. The network incorporates the reward signals from both $D_a$ and $D_c$. The signal from $D_a$ is used to push $\pi_\theta$ closer to $\pi_+$, while the signal $D_c$ separates $\pi_\theta$ and $\pi_-$. The loss function can be defined as:

$$\min_{\pi_\theta} \omega_\alpha (\mathbb{E}_{\rho_{\pi_\theta}}[\log(1 - D_a(s, a))]) - \omega_\beta (\mathbb{E}_{\rho_\theta}[\log(D_c(s, a))]) - \lambda H(\pi_\theta)$$

where $H(\pi)$ is the casual entropy of the policy, which encourages diversity in the learned policy, and $\lambda \geq 0$ is a parameter that is used to control $H(\pi_\theta)$. The parameters $\omega_\alpha$ and $\omega_\beta$ are weights with values between 0 and 1, and balance the reward signals.

The adversarial discriminator $D_a$, the cooperative discriminator $D_c$, and the policy network $\pi_\theta$ are trained in a three-party min-max game, which can be defined as:

$$\min_{pi_\theta, D_c} \max_{D_a} \omega_a (\mathbb{E}_{\rho_{\pi_\theta}}[\log(1 - D_a(s, a))] + \mathbb{E}_{\rho_{\pi_+}}[\log(D_a(s, a))]) -$$
$$\omega_\beta (\mathbb{E}_{\rho_{\pi_\theta}, \rho_{\pi_+}}[\log(D_c(s, a))] + \mathbb{E}_{\rho_{\pi_-}}[\log(1 - D_c(s, a))]) - \lambda H(\pi_\theta)$$

where $\omega_a$ and $\omega_b$ are weight parameters that weight the contribution of the adversarial discriminator and the cooperative discriminator. The entropy of the policy $\pi_\theta$ encourages policy diversity, and is defined as:

$$H(\pi_\theta) \triangleq \mathbb{E}_{\pi_\theta}[-\log \pi_\theta(a|s)]$$

When both $D_a$ and $D_c$ are optimized, the outcome of the three-party min-max game is equivalent to the following optimization problem:

$$\min_{\pi_\theta} D_{JS}(\rho_{\pi_+} \| \rho_{\pi_\theta}) - D_{JS}((\rho_{\pi_+} + \rho_{\pi_\theta}) \| \rho_{\pi_-}) - \lambda H(\pi_\theta)$$

which finds a policy whose occupancy measure minimizes the JS divergence to $\pi_+$ and maximizes the JS divergence to $\pi_-$.

Referring now to FIG. 4, pseudo-code of the learning process for an ACIL model is shown. First the patient model $G_w$ is trained, followed by iterative training of $D_a$, $D_c$, and $\pi_\theta$.

In tests, the present embodiments generated policies that substantially outperformed baseline processes for generating treatment trajectories. ACIL considers discovering DTRs as a sequential decision-making problem and focuses on the long-term influence of the current action. Additionally, with the use of both positive and negative trajectory examples as training data, ACIL is able to mimic policies that have positive health outcomes, while avoiding mistakes. The result is a superior treatment policy, that responds to changing patient conditions in a manner that maximizes the likelihood of a positive health outcome.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

As employed herein, the term "hardware processor subsystem" or "hardware processor" can refer to a processor, memory, software or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), field-programmable gate arrays (FPGAs), and/or programmable logic arrays (PLAs).

These and other variations of a hardware processor subsystem are also contemplated in accordance with embodiments of the present invention.

Figure 5:
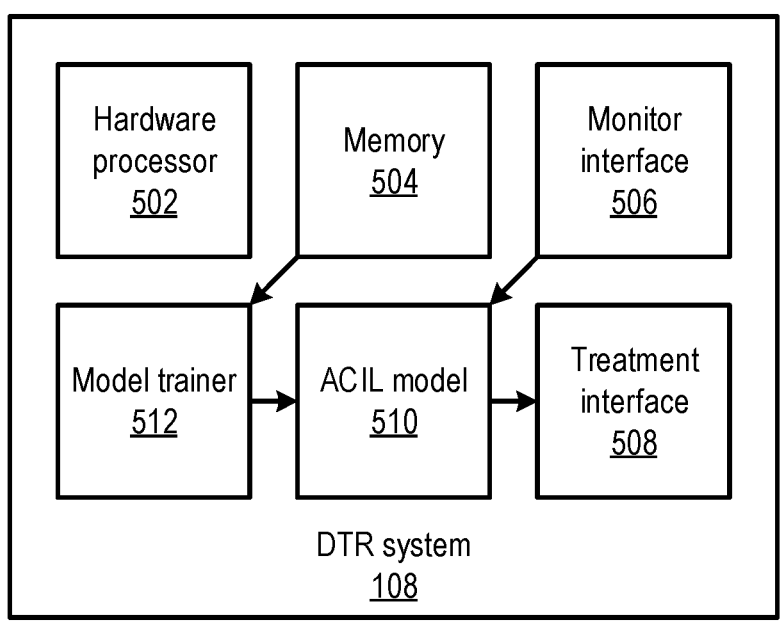
FIG. 5 is a block diagram of a dynamic treatment regime system that generates and implements a dynamic treatment regime, in accordance with an embodiment of the present invention.

Referring now to FIG. 5, additional detail on the DTR system 108 is shown. The system 108 can include a hardware processor 502, and memory 504 that is coupled to the hardware processor 502. A monitor interface 506 provides communications between the DTR system 108 and the patient monitor 106, while a treatment interface provides communications between the DTR system 108 and the treatment application system 110.

It should be understood that the interfaces 106 and 110 can each include any appropriate wired or wireless communications protocol and medium. In some embodiments, the DTR system 108 may be integrated with one or both of the patient monitor 106 and the treatment application system 110, such that the interfaces 106 and 110 represent internal communications, such as buses. In some embodiments, one or both of the patient monitor 106 and the treatment application system 110 can be implemented as separate, discrete pieces of hardware, that communicate with the DTR system 108.

The DTR system 108 may include one or more functional modules. In some embodiments, such modules can be implemented as software that is stored in memory 504 and that is executed by hardware processor 502. In other embodiments, such modules can be implemented as one or more discrete hardware components, for example implemented as application-specific integrated chips or field programmable gate arrays.

During operation, patient information is received through the monitor interface 506. In some embodiments, this information may be received as discrete sensor readings from a variety of sensors 104. In other embodiments, this information may be received from the patient monitor 106 as a consolidated vector that represents multiple measurements.

Some patient information may also be stored in the memory 504, for example in the form of patient demographic information and medical history.

The ACIL model 510 uses the collected patient information to generate a treatment trajectory. This trajectory is updated as new patient information is received. The treatment interface 508 sends information about the treatment trajectory to the treatment application system 110, for use with the patient.

In some embodiments, the ACIL model 510 may be implemented with one or more artificial neural networks. These networks are trained, for example in the manner described above, using model trainer 512. Model trainer uses a set of training data, which may be stored in memory 504, and which may include treatment trajectories that resulted in positive health outcomes, as well as treatment trajectories that resulted in negative health outcomes.

An artificial neural network (ANN) is an information processing system that is inspired by biological nervous systems, such as the brain. The key element of ANNs is the structure of the information processing system, which includes a large number of highly interconnected processing elements (called "neurons") working in parallel to solve specific problems. ANNs are furthermore trained in-use, with learning that involves adjustments to weights that exist between the neurons. An ANN is configured for a specific application, such as pattern recognition or data classification, through such a learning process.

Figure 6:
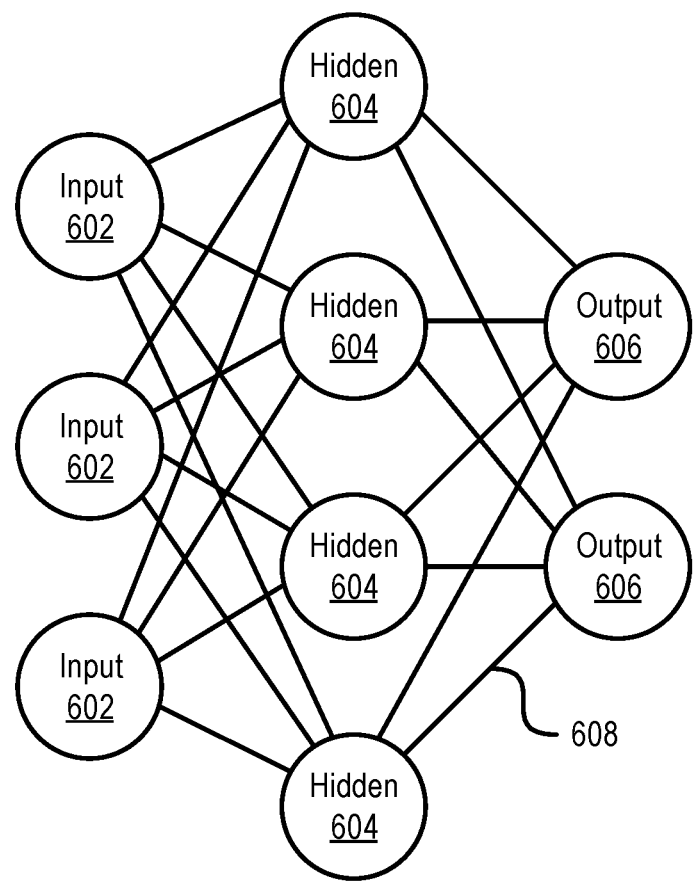
FIG. 6 is a diagram of an exemplary neural network structure, in accordance with an embodiment of the present invention.

Referring now to FIG. 6, a generalized diagram of a neural network is shown. ANNs demonstrate an ability to derive meaning from complicated or imprecise data and can be used to extract patterns and detect trends that are too complex to be detected by humans or other computer-based systems. The structure of a neural network is known generally to have input neurons 602 that provide information to one or more "hidden" neurons 604. Connections 608 between the input neurons 602 and hidden neurons 604 are weighted and these weighted inputs are then processed by the hidden neurons 604 according to some function in the hidden neurons 604, with weighted connections 608 between the layers. There may be any number of layers of hidden neurons 604, and as well as neurons that perform different functions. There exist different neural network structures as well, such as convolutional neural network, maxout network, etc. Finally, a set of output neurons 606 accepts and processes weighted input from the last set of hidden neurons 604.

This represents a "feed-forward" computation, where information propagates from input neurons 602 to the output neurons 606. Upon completion of a feed-forward computation, the output is compared to a desired output available from training data. The error relative to the training data is then processed in "feed-back" computation, where the hidden neurons 604 and input neurons 602 receive information regarding the error propagating backward from the output neurons 606. Once the backward error propagation has been completed, weight updates are performed, with the weighted connections 608 being updated to account for the received error. This represents just one variety of ANN.

Figure 7:
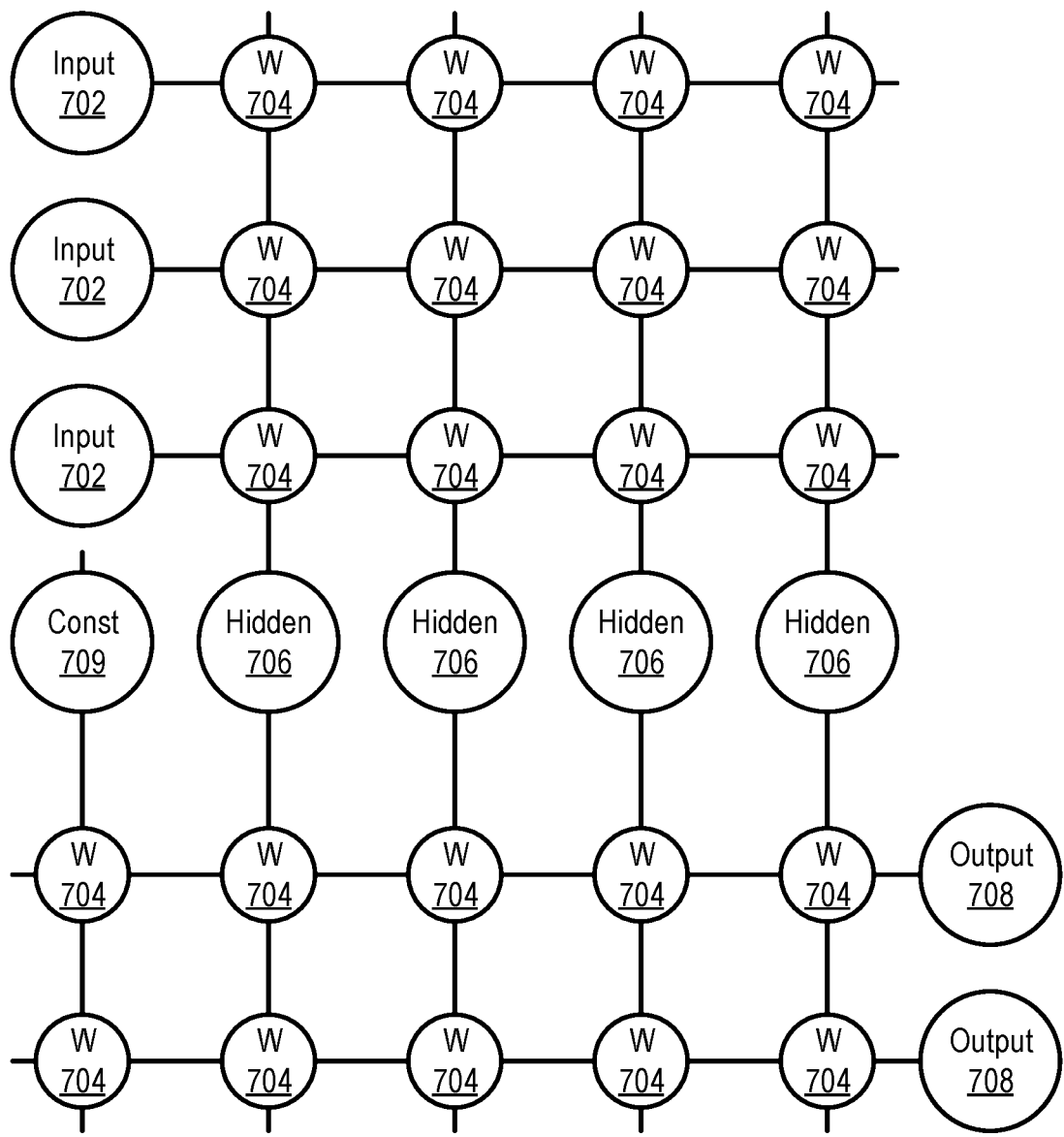
FIG. 7 is a diagram of an exemplary neural network structure with weights, in accordance with an embodiment of the present invention.

Referring now to FIG. 7, an ANN architecture 700 is shown. It should be understood that the present architecture is purely exemplary, and that other architectures or types of neural network may be used instead. The ANN embodiment described herein is included with the intent of illustrating general principles of neural network computation at a high level of generality and should not be construed as limiting in any way.

Furthermore, the layers of neurons described below and the weights connecting them are described in a general manner and can be replaced by any type of neural network layers with any appropriate degree or type of interconnectivity. For example, layers can include convolutional layers, pooling layers, fully connected layers, softmax layers, or any other appropriate type of neural network layer. Furthermore, layers can be added or removed as needed and the weights can be omitted for more complicated forms of interconnection.

During feed-forward operation, a set of input neurons 702 each provide an input signal in parallel to a respective row of weights 704. The weights 704 each have a respective settable value, such that a weight output passes from the weight 704 to a respective hidden neuron 706 to represent the weighted input to the hidden neuron 706. In software embodiments, the weights 704 may simply be represented as coefficient values that are multiplied against the relevant signals. The signals from each weight adds column-wise and flows to a hidden neuron 706.

The hidden neurons 706 use the signals from the array of weights 704 to perform some calculation. The hidden neurons 706 then output a signal of their own to another array of weights 704. This array performs in the same way, with a column of weights 704 receiving a signal from their respective hidden neuron 706 to produce a weighted signal output that adds row-wise and is provided to the output neuron 708.

It should be understood that any number of these stages may be implemented, by interposing additional layers of arrays and hidden neurons 706. It should also be noted that some neurons may be constant neurons 709, which provide a constant output to the array. The constant neurons 709 can be present among the input neurons 702 and/or hidden neurons 706 and are only used during feed-forward operation.

During back propagation, the output neurons 708 provide a signal back across the array of weights 704. The output layer compares the generated network response to training data and computes an error. The error signal can be made proportional to the error value. In this example, a row of weights 704 receives a signal from a respective output neuron 708 in parallel and produces an output which adds column-wise to provide an input to hidden neurons 706. The hidden neurons 706 combine the weighted feedback signal with a derivative of its feed-forward calculation and stores an error value before outputting a feedback signal to its respective column of weights 704. This back propagation travels through the entire network 700 until all hidden neurons 706 and the input neurons 702 have stored an error value.

During weight updates, the stored error values are used to update the settable values of the weights 704. In this manner the weights 704 can be trained to adapt the neural network 700 to errors in its processing. It should be noted that the three modes of operation, feed forward, back propagation, and weight update, do not overlap with one another.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment. However, it is to be appreciated that features of one or more embodiments can be combined given the teachings of the present invention provided herein.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended for as many items listed.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A method for responding to changing conditions, comprising:
    training a model, using a processor, including trajectories that resulted in a positive outcome and trajectories that resulted in a negative outcome, by using an adversarial discriminator to train the model to generate trajectories that are similar to historical trajectories that resulted in a positive outcome, and by using a cooperative discriminator to train the model to generate trajectories that are dissimilar to historical trajectories that resulted in a negative outcome, and including iteratively training the adversarial discriminator, the cooperative discriminator, and the dynamic response regime using a three-party optimization;
    generating a dynamic response regime using the trained model and environment information; and
    responding to changing environment conditions in accordance with the dynamic response regime.

2. The method of claim 1, wherein the historical trajectories that resulted in a positive outcome and the historical trajectories that resulted in a negative outcome include patient treatment trajectories.

3. The method of claim 2, wherein the positive outcomes are positive patient health outcomes, and the negative outcomes are negative patient health outcomes.

4. The method of claim 2, wherein the environment information and the environment conditions reflect information about a patient being treated.

5. The method of claim 1, wherein the adversarial discriminator, the cooperative discriminator, and the dynamic response regime are implemented as multiple-layer perceptrons.

6. The method of claim 1, wherein training the model comprises training an environment model that encodes environment information as a vector in a latent space.

7. The method of claim 6, wherein the model is implemented as a variational auto-encoder network.

8. The method of claim 1, wherein responding to changing environment conditions comprises automatically performing a responsive action to correct a negative condition.

9. A system for responding to changing conditions, comprising:
    a machine learning model, configured to generate a dynamic response regime for using environment information;
    a model trainer, configured to train the machine learning model, including trajectories that resulted in a positive outcome and trajectories that resulted in a negative outcome, by using an adversarial discriminator to train the machine learning model to generate trajectories that are similar to historical trajectories that resulted in a positive outcome, and by using a cooperative discriminator to train the model to generate trajectories that are dissimilar to historical trajectories that resulted in a negative outcome, and to iteratively train the adversarial discriminator, the cooperative discriminator, and the dynamic response regime using a three-party optimization; and
    a response interface, configured to trigger a response to changing environment conditions in accordance with the dynamic response regime.

10. The system of claim 9, wherein the historical trajectories that resulted in a positive outcome and the historical trajectories that resulted in a negative outcome include patient treatment trajectories.

11. The system of claim 10, wherein the positive outcomes are positive patient health outcomes, and the negative outcomes are negative patient health outcomes.

12. The system of claim 9, wherein the environment information and the environment conditions reflect information about a patient being treated.

13. The system of claim 9, wherein the adversarial discriminator, the cooperative discriminator, and the dynamic response regime are implemented as multiple-layer perceptrons in the machine learning model.

14. The system of claim 9, wherein the model trainer is further configured to train an environment model that encodes the environment information as a vector in a latent space.

15. The system of claim 14, wherein the environment model is implemented as a variational auto-encoder network in the machine learning model.

16. The system of claim 9, wherein the response interface is further configured to automatically perform a responsive action to correct a negative condition.

* * * * *